(12) United States Patent
Green et al.

(10) Patent No.: US 7,933,011 B2
(45) Date of Patent: Apr. 26, 2011

(54) FIBER OPTIC DETECTION SYSTEM

(75) Inventors: Douglas Jason Green, Baltimore, MD (US); Jordan Fields, San Antonio, FL (US)

(73) Assignee: Smiths Detection Inc., Edgewood, MD (US)

( * ) Notice: Subject to any disclaimer, the term of this patent is extended or adjusted under 35 U.S.C. 154(b) by 212 days.

(21) Appl. No.: 12/172,142

(22) Filed: Jul. 11, 2008

(65) Prior Publication Data

US 2009/0079975 A1 Mar. 26, 2009

Related U.S. Application Data

(60) Provisional application No. 60/929,802, filed on Jul. 12, 2007.

(51) Int. Cl.
*G01N 21/01* (2006.01)

(52) U.S. Cl. ..................................................... 356/244

(58) Field of Classification Search .................. None
See application file for complete search history.

(56) References Cited

U.S. PATENT DOCUMENTS

| 6,369,893 | B1 | 4/2002 | Christel et al. |
| 2006/0177841 | A1 | 8/2006 | Wangh et al. |

*Primary Examiner* — Gregory J Toatley
*Assistant Examiner* — Amanda H Merlino
(74) *Attorney, Agent, or Firm* — Foley & Lardner LLP

(57) ABSTRACT

A sealed and decontaminated fiber optic detection apparatus includes an optics portion with individual chambers. Each chamber housing optical and electro-optical components. A manifold accommodates fibers, with each of the fibers being in optical communication with the optical and electro-optical components of a corresponding chamber. The apparatus also includes a sample holder that holds a sample to be tested and a mounting device provided between the sample holder and the manifold. The mounting device and the manifold form a sealed fiber optic interface between the sample holder and the optics portion.

21 Claims, 3 Drawing Sheets

FIBER OPTIC DETECTION SYSTEM

BACKGROUND

The management of biological threats require the development of detection techniques that are rapid, sensitive, and reliable. Polymerase chain reaction (PCR) has emerged as a leading detection tool in determining whether a particular threat is present. PCR is used to detect the presence of a specific nucleic acid strand in a sample. By detecting specific nucleic acid strands, biological organisms can be identified. For example, checking a sample for a DNA strand specific for smallpox allows a user to determine whether or not smallpox is present in a sample. Fluorescent probes are often used to detect the presence of a specific nucleic acid strand in a sample. The presence and/or amount of the target nucleic acid can be determined by measuring the fluorescence from the sample. Optical detection systems are also used with techniques other than PCR to detect the presence of an analyte in a sample.

Additionally, immunological methods also are known for detecting the presence of a biological analyte of interest.

Generally, this technology has been implemented in a laboratory environment requiring samples to be collected remotely and then sent to a central laboratory for preparation and analysis. This shipment of suspected samples between the field and the laboratory can cause transportation delays and incurs the risk of further contamination. A major obstacle in implementing field usable instruments is developing instruments that can be successfully decontaminated. More specifically, many instruments have sensitive electrical and optical components that would be damaged by standard decontamination procedures.

Current instruments, even portable ones, can not be used where needed, due to the inability of the instruments to be fully decontaminated. Even when an instrument is used in a so called "clean area," doubts exits about whether the device was contaminated. This is largely due to the fact that the optical and electro-optical components are often very sensitive and cannot be fully decontaminated.

Therefore, the need arises for an instrument that provides accurate measurements of analytes under varying environmental conditions and variations in samples that is both portable and easily decontaminated.

SUMMARY OF THE DISCLOSURE

Accordingly, a solution to the problems described above is provided.

According to one embodiment, a sealed and decontaminated fiber optic detection apparatus includes an optics portion with individual chambers. Each chamber housing optical and electro-optical components. A manifold accommodates fibers, with each of the fibers being in optical communication with the optical and electro-optical components of a corresponding chamber. The apparatus also includes a sample holder that holds a sample to be tested and a mounting device provided between the sample holder and the manifold. The mounting device and the manifold form a sealed fiber optic interface between the sample holder and the optics portion.

According to another embodiment, a method for creating a sealed and decontaminated fiber optic detection apparatus includes housing optical and electro-optical components in individual chambers of an optics portion and accommodating one end of fibers which are in optical communication with the optical and electro-optical components, in a manifold. The method also includes providing a sample holder that holds a sample to be tested, accommodating the other end of the fibers between the sample holder and the manifold and forming a sealed fiber optic interface between the sample holder and the optics portion.

DETAILED DESCRIPTION

A fiber optic detection apparatus and method for its use and construction are disclosed. The following description describes some exemplary embodiments. However, additional embodiments will be readily apparent to one of skill in the art based on the description of the exemplary embodiments. In other instances, well-known structures and devices are shown in block diagram form, rather than in detail. One of skill in the art is readily able to construct and use devices performing the functions described in the block diagram form.

Figure 2:
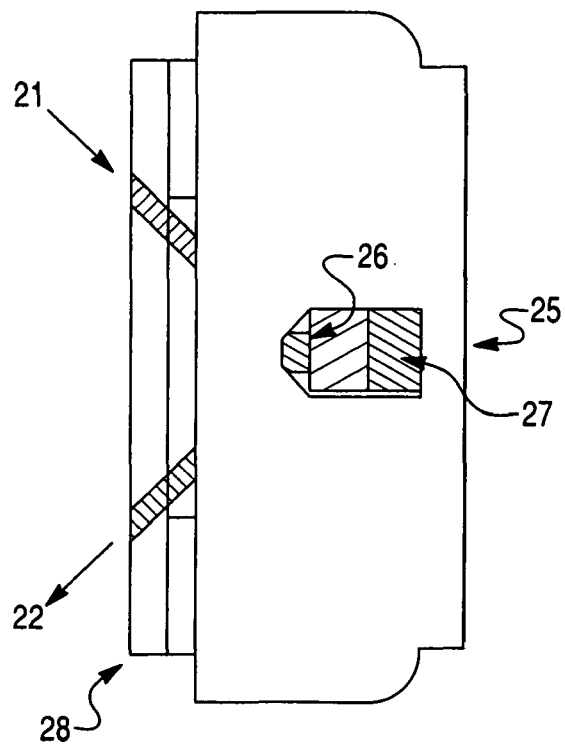
FIG. 2 illustrates a fiber arrangement and sample for the sealed and decontaminated fiber optic detection apparatus in accordance with an embodiment.
Figure 3:
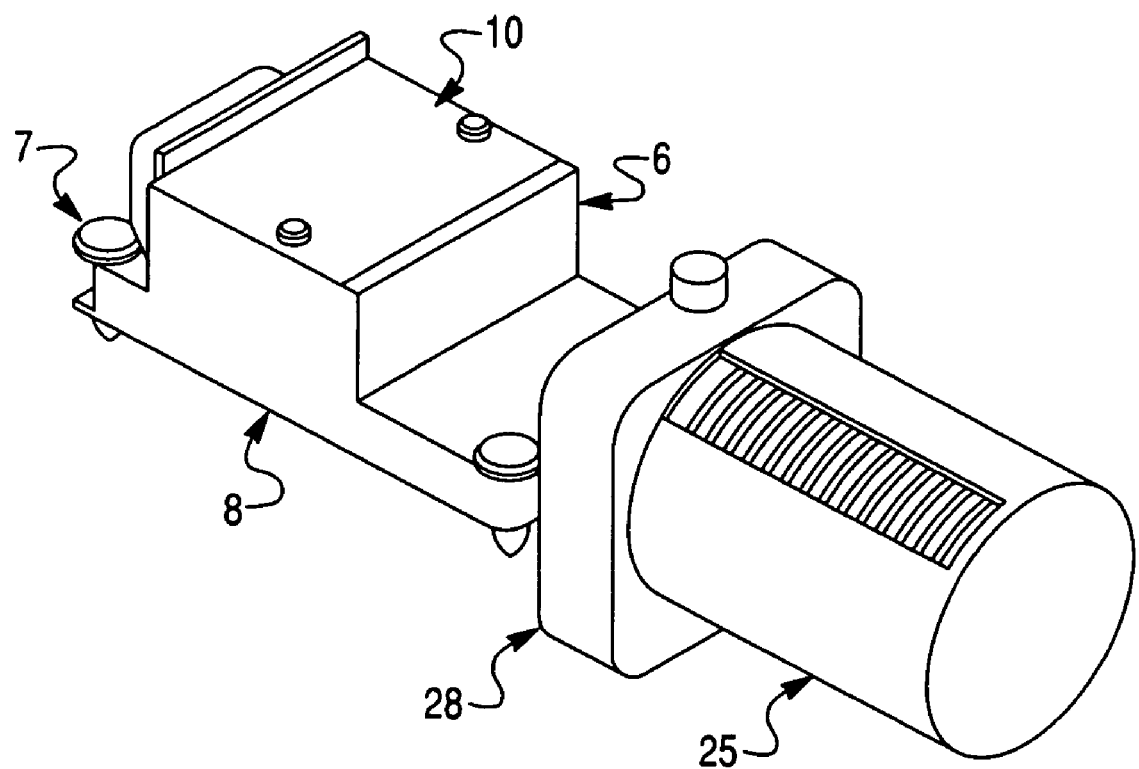
FIG. 3 illustrates a perspective view of the sealed and decontaminated fiber optic detection apparatus in accordance with an embodiment.

FIGS. 2 and 3 show an exemplary fiber optic detection apparatus. FIG. 3 shows an exemplary fiber optic detection apparatus comprising an optics block 10, a housing 8, a fiber manifold 6, a mounting device 7, mounting block 28, and heat sink 25. As can be better seen from FIG. 2, the fiber optic detection apparatus can also include a heat sink 25, sample holder 26, and thermoelectric coolers 27. However, a fiber optic detection apparatus does not require each and every one of these components. For example, a fiber optic detection apparatus can comprise an optics block 10, a housing 8, a fiber manifold 6, a mounting device 7, mounting block 28, and heat sink 25, sample holder 26. An exemplary fiber optic detection apparatus is discussed in greater detail below.

Figure 1:
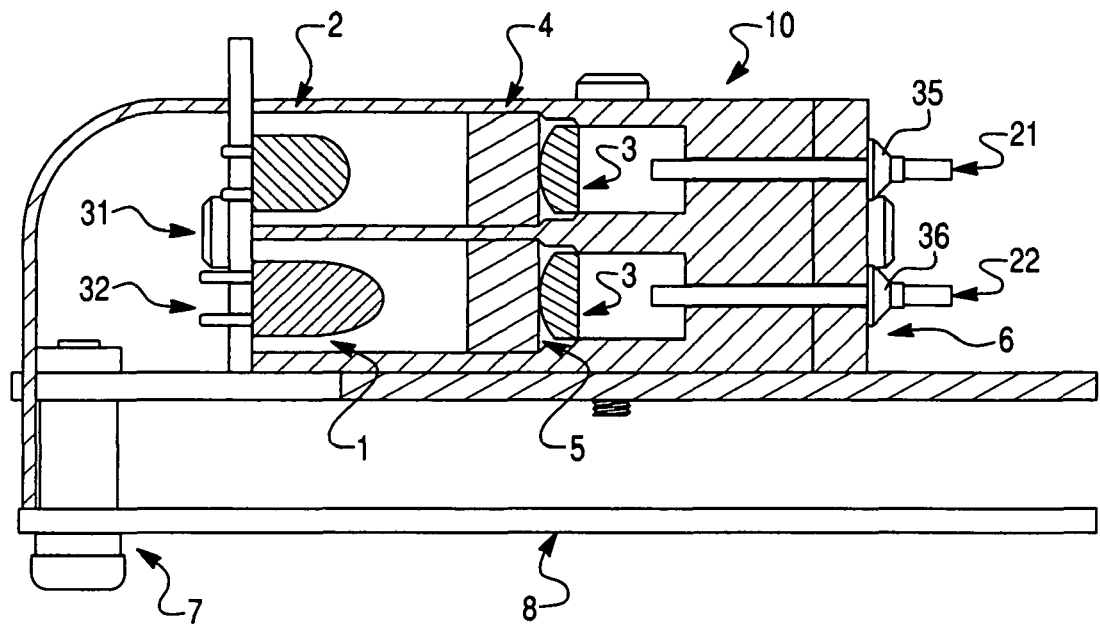
FIG. 1 illustrates an optics block for the sealed and decontaminated fiber optic detection apparatus in accordance to an embodiment.

FIG. 1 illustrates an optics block for the fiber optic detection apparatus in accordance with an embodiment. The optics block, generally noted by reference numeral 10, can include a light source 1, a light detector 2, an emission filter 4, an excitation filter 5, and lenses 3. FIG. 1 shows a light source 1, excitation filter 5, and one lens 3 in a excitation chamber 32, and the light detector 2, emission filter 4, and a lens 3 in a separate emission chamber 31. The components for generating light to send to a sample (light source 1, excitation filter 5, and lens 3 in FIG. 1) are generally referred to as "source components." The components for detecting light to from a sample (light detector 2, emission filter 4, and a lens 3 in FIG. 1) will generally be referred to as "emission components." FIG. 1 shows source components and emission components in separate chambers, the excitation chamber 32 and emission chamber 31. This generally allows the components to be easily aligned and makes maintenance and replacement of specific components easier. In some embodiments, however, these components can be part of the same chamber. Optical and electro-optical components other than the ones specifically illustrated can be provided to enhance optical communication. Also, an optics block does not need to have each of these components. For example, if a laser is used as light source 1, excitation filter 5 may not be necessary, because the laser emits light at a very narrow wavelength interval.

The optics block 10 can be single-channeled or multi-channeled. A single-channeled optics block includes optical and electro-optical components capable of detecting the intensity of one wavelength at a time. On the other hand, a multi-channeled optics block includes optical and electro-optical components capable of detecting more than one wavelength at a time. In practice, multi-channeled devices can be used, for example, to simultaneously detect the presence and quantity of one or more analytes identified by monitoring light emitted or absorbed at more than one wavelength.

In some embodiments, the optics-block can be single-channeled. In other embodiments, the optics block can have two, three, four, or more channels. The number of channels can be increased by adding additional excitation chambers and/or emissions chambers. For example, a two channeled device may have two emissions chambers and two excitation chambers. A two channeled device can also have two excitation chambers and a single emission chamber adapted to detect more than one wavelength of light. In some embodiment, the optics block is four-channeled with each channel having a separate emission chamber 31 and excitation chamber 32. Such a four-channeled optics block can have eight fibers, one for each of the emission chambers 31 and excitation chambers 32. In some embodiments, the source components and emission components for each channel are housed in a separate chamber.

FIG. 1 shows an optics block with two chambers, one chamber for the source components (excitation chamber 32) and another chamber for the emission components (emission chamber 31). However, as discussed above, the optics block 10 can have a single chamber or a single chamber for each channel. For example, a four channel optics block can have four emission chambers 31 each housing emission components and four excitation chambers 32 each housing source components. In another embodiment, a four channel optics block can have four different chambers each housing the components for one of the channels. In yet another embodiment, a four channel optics block can have only a single chamber housing the components for all four channels. However, separate chambers for each set of source and emission components can be preferable for certain application, because it can allow for better alignment of the components.

As discussed in detail below, the fibers through which light is transmitted can be coupled to the optics block through a manifold 6. Because the source components and emission components are all housed in the optics block, separate from the other components of the fiber optic detection apparatus, the optics block 10 can be constructed so that it can be readily decontaminated and kept separate from sample. For example, the optics block 10 can be housed in a material that is easily decontaminated. The material can be any suitable material, such a metal or plastic. This is an useful characteristic, because it allows the fiber optic detection apparatus to be decontaminated and routinely cleaned without risk of damaging or otherwise adversely affecting the optical components.

Any suitable light source can be used for light source 1. According to an embodiment, the light source 1 can be a light emitting diode (LED). By way of example, light source 1 can also take the form of a laser, laser diode, photodiode, or a lamp. Examples of suitable lamps include, but are not limited to, xenon arc lamps, mercury vapor lamps, flashlamps, or arc lamps. Alternatively, a plurality of light sources, either of the same type or of a different type can be provided to generate an excitation light of sufficient intensity, for example. For example, a plurality of LEDs may be used for light source 1.

Any detector that is suitable for detecting the desired wavelength of light can be used for light detector 2. According to one embodiment, light detector 2 can be a photodiode. The light detector 2 can also be, for example, a photodetector, a photomultiplier tube, avalanche diode, charge-coupled device, or any other light detector known in the art. The light detector 2 be either a single-channeled or multichanneled detector. A single-channeled detector can only detect the intensity of one wavelength at a time, while a multichanneled can detect the intensity at more than one wavelength simultaneously.

Any lens that is suitable for focusing light as desired can be used for lens 3. In one embodiment, lens 3 can be a PCX lens. However, the lens 3, is not limited to being a PCX lens, but may be any type of lens used to sufficiently focus light. For example, any optical collimating device, such as a collimating lens, could be utilized with the invention. Lens 3 in the emission chamber 3 and excitation chamber 2 can be the same or different. For example, lens 3 in excitation chamber 32 can be a PCX lens, and lens 3 in the emission chamber 31 can be a lens other than a PCX lens.

Any filter or monochromator that is suitable for passing the desired wavelengths of light can be used for excitation filter 5 and emission filter 4. For example, these filters can be bandpass filters and interference filters. Bandpass filters transmit light with a wavelength either greater than or lesser than a given wavelength, and interference filters are filters that transmit light in a given wavelength interval. In some embodiments, excitation filter 5 or emission filter 4 will be a combination of two or more filters or monochromators. For example, excitation filter 5 and emission filter 4 can be a combination of two bandpass filters. In some embodiments, excitation filter 5 or emission filter 4 are not present. For example, the use of laser, which emits light with a narrow wavelength distribution, may obviate the need for an excitation filter 5. As another example, an emission filter 4 may not be necessary depending on the light detector 2 used.

As can be seen from FIG. 1, excitation fiber 22 and source fiber 21 can be coupled to the optics block 10 using a manifold 6. Manifold 6 can be provided at an end portion of the optics block 10, sealing the excitation and emission chambers. According to one embodiment, the manifold 6 is preassembled with the fibers 21 and 22 to avoid errors in fiber connections. The manifold 6, which can be detachably mounted using various attachment mechanisms, for example, allows for easy assembly and maintenance of the optics block 10. Alternatively, the manifold 6 can be sealed to the end portion of the optics block 10, for example. The manifold 6 is detachably mounted or sealed such that the optical and electro-optical components in the optics block are not contaminated during operation of the fiber optic detection apparatus. The excitation and source fibers can be coupled to the manifold 6 with coupling devices 35 and 36. The coupling devices 35 and 36 also help ensure that the optical and electro-optical components remain contaminate-free. The fiber optic apparatus can have a different fiber for each set of source components and emission components. For example, a four channel device can have eight fibers (four excitation fibers and four emission fibers), a pair for each channel.

Generally, a fiber optic detection apparatus has source components for generating light to be directed to a sample and excitation components for detecting light emitted by the sample. The light can be directed from the source components to a sample and from the sample to the excitation components using optical fibers.

According to one embodiment, light source 1, excitation filter 5, one of the lenses 3 and an excitation fiber 22 constitute the excitation portion of the optics block 10. Light source 1, excitation filter 5 and lens 3 can be used to focus light on an aperture of the excitation fiber 22. According to one embodiment, excitation fiber 22 may be a 1500 micron solid fiber, for example. The excitation fiber 22 can be used to direct the light to a sample. Light emitted from the sample can then be collected by the source fiber 21 and directed to the emission portion of the optics block 10. In some embodiments, the source fiber 21 and excitation fiber 22 are at an angle of 90 degrees to one another. Placing the source fiber 21 at a 90 degree angle to excitation fiber 22 can prevent light from the source fiber 21 from being detected by excitation fiber 22 thereby reducing interference and noise. The emission portion of the optics block 10 includes source fiber 21 (which can be substantially similar to excitation fiber 22), emission filter 4, lens 3 and light detector 2.

The optics block 10 can be mounted on a housing for use in operation. In one embodiment shown in FIG. 3, the optics block 10 is provided on a housing 8 and secured by a mounting device 7 in a manner not to interfere with the operation of the optical and electro-optical components. The housing 8 can be any suitable material in any suitable configuration. Mounting device 7 can be any suitable device for fixing the optics block 10 to housing 8. In some embodiments, mounting device 7 removably fixes optics block 10 to housing 8. For example, mounting device 7 can be a screw, thumb screw, bolt, or clamp. In some embodiments, mounting device 7 permanently or semi-permanently fixes optics block 10 to housing 8. For example, mounting device 7 can be a rivet or weld.

The optics block 10 is in optical communication with a sample. The optical communication can be by way of optical fibers, such as excitation fiber 22 and source fiber 21. In one embodiment shown in FIG. 2, source fiber 21 and excitation fiber 22 can be routed to a sample holder 26, such as a cuvette, at an angle of 90 degrees through a cutout in the thermally conductive sample holder 26. In other embodiments, the alignment between the fiber and the cutout may be 0, 180, or 270 degrees. In some embodiments, thermoelectric coolers 27 can be provided between a mounting block 28 and a heat sink 25. This arrangement of the fibers 21 and 22 allows for optical interrogation of a sample to take place from one side while heating and cooling action using the thermoelectric coolers 27 and heat sink 25, is performed on the other side.

According one embodiment, the sealed fiber optic detection apparatus is a fluorimeter apparatus, used for a polymerase chain reaction (PCR) in conjunction with a thermocycler used from DNA analysis. Fluorescence is a physical phenomenon based upon the ability of some molecules to absorb light energy at specified wavelengths (excitation frequency) and then emit light energy of a longer wavelength and at a lower energy (emission frequency). This is referred to as fluorescence if the emission is relatively long-lived, typically on the order of $10^{11}$ to $10^7$ seconds. Substances able to fluoresce share and display a number of common characteristics: they absorb light energy at one wavelength or frequency to reach a "singlet", an excited energy state, and subsequently emit light at another light frequency, returning to a "ground" energy level.

As illustrated in FIG. 2, a set including the source fiber 21 and the excitation fiber 22 is used for each fluorescent analyte being probed. Thus, according to one embodiment, light source 1, excitation filter 5, one of the lenses 3 and the excitation fiber 22, constituting the excitation portion of the optic block 10, focus light on an aperture of the proximal end of excitation fiber 22. The light propagates along the length of excitation fiber 22 and a portion of this propagated light exits the distal end of the excitation fiber 22 and is absorbed by one or more light energy absorbing dyes of the sample, for example, stored in the sample holder 26. The light energy absorbing dye may or may not be immobilized, may or may not be directly attached to the excitation fiber 22 itself, may or may not be suspended in a fluid sample containing one or more analytes of interest to be detected, and may or may not be retainable for subsequent use in a second optical determination, for example.

The fluorimeter can be set up to use any dye, such as the light energy absorbing dye mentioned above. The light energy absorbing dye may be customized for the specific application of the fluorimeter, such as PCR. Other applications for which a customizable dye or taggant may be utilized include, but are not limited to, immunoassays and general chemical assays. Other embodiments of the fluorimeter may utilize target samples, instead of customizable dyes or taggants, that contain compounds such as chlorophyll, fluorescein, and rhodamine, for example.

Because the fluorimeter can be utilized in the field as opposed to a formal laboratory setting, the fluorimeter could be utilized to detect chemical weapons or pathogens, for example. The flourimeter can also be utilized for waste water tracking, part inspection, and genetic tracing, among other applications.

In return, once the dye (or taggant or target) has absorbed the light energy, some light energy of varying wavelength and intensity returns through the proximal end of source fiber 21 and is then conveyed to the remainder of the components that make up the sample portion. That is, light from source fiber 21 is focused on emission filter 4 and lens 3 and then collected into the light detector 2 where the emerging light energy is observed and measured.

Use of a separate sample portion and a separate excitation portion can signal amplitude loss that can occur by signal splitting t using a bifurcated fiber. In another embodiment, a bifurcated fiber could be utilized. For example, a 32 stranded fiber bundle could be utilized. The bundle could be indiscriminatorily halved, with one group (16 fibers) of the bundle plugged into the source section and the other group (remaining 16 strands) plugged into the emitter section. Instead of two separate source and emitter strands, one strand can point at the fluorescence that is trying to be measured, resulting h in retroflective fluorescence.

According to an embodiment, the sample holder 26 is made of a conductive material such as aluminum and includes the cutout. The cutout may, for example, include an optical window. The cutout for the optical window is positioned at a bottom location of the reagent tube of the sample holder 26 to alleviate any problem with maintaining uniform heating of the sample holder 26. In a preferred embodiment, the sample holder may hold a volume of 20 microliters. A small sample volume is preferred, because the sample must both be heated and optically interrogated. Thus, in order to obtain the best measurements, it is ideal to surround the sample with as much copper as possible while still allowing for holes for the fibers to see the plastic of the sample. Again, various alignments between the sample and the fiber possible.

FIG. 3 illustrates a perspective view of the fiber optic detection apparatus in accordance to one embodiment. The fiber optic detection includes the housing 8 which accommodates optics block 10 and manifold 10. The heat sink 25 and mounting block 28 are provided adjacent to the housing 8. Although not shown, fibers are routed between the mounting block 28 and the manifold 6. According to one embodiment, the fibers are mounted at each end with some type of adhesive such as, for example, an epoxy. Also according to one embodiment, the mounting block 28 and the heat sink 25 are designed for full immersion for decontamination. Furthermore, the mounting block 28 can be mounted to any flat bulkhead structure allowing flexibility with different final packaging schemes.

Figure 4:
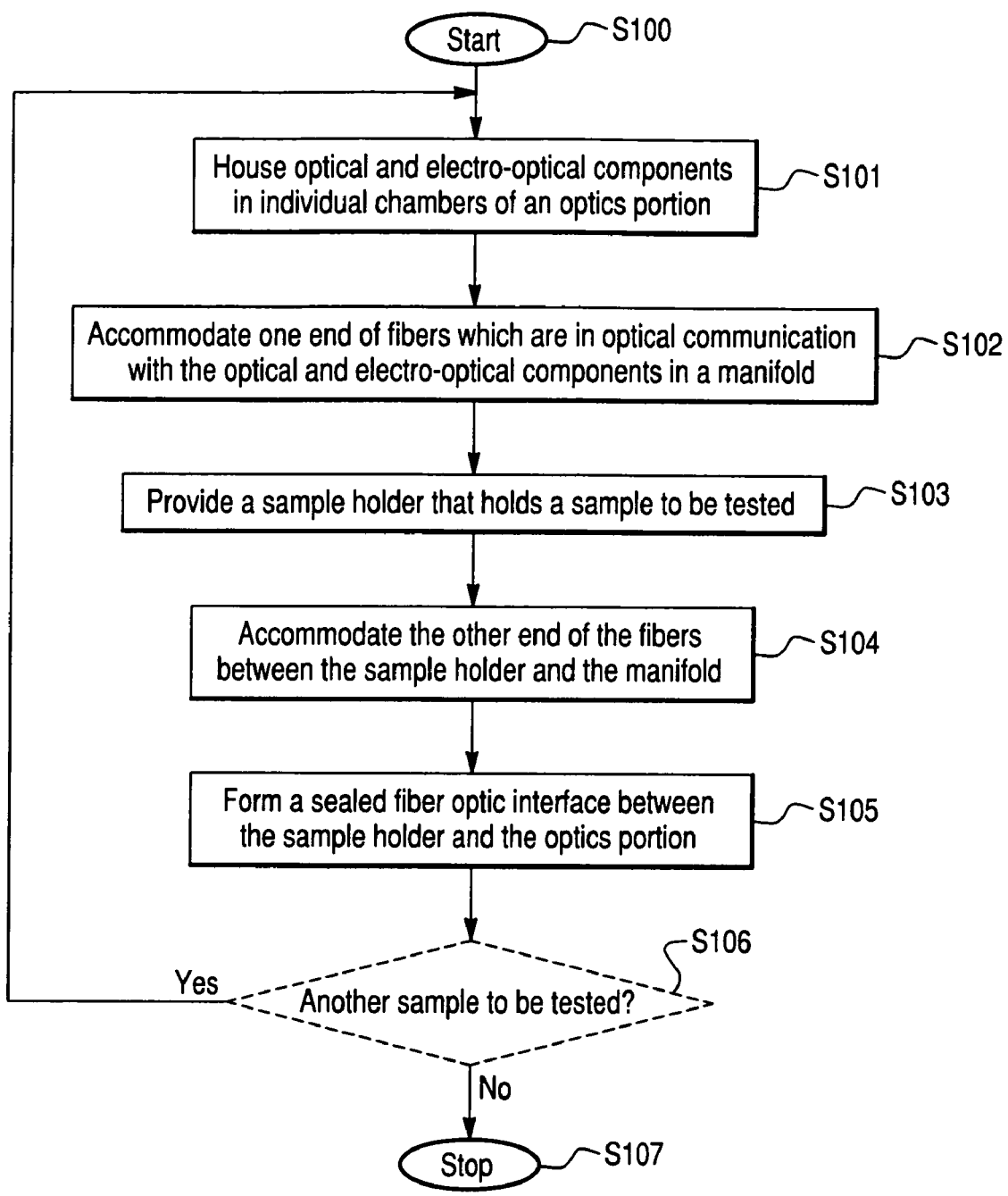
FIG. 4 is a flowchart depicting steps performed for creating a sealed and decontaminated fiber optic detection apparatus in accordance with an embodiment.

FIG. 4 is a flowchart depicting steps performed in creating a sealed and decontaminated fiber optic detection apparatus in accordance with one embodiment. The process begins from a start state S100 and proceeds to process step S101, where optical and electro-optical components are housed in individual chambers of an optics portion. At process step S102, one end of fibers which are in optical communication with the optical and electro-optical components, are accommodated in a manifold. At process step S103, a sample to be tested is housed in a sample holder. At process step S104, the other end of the fibers are accommodated between the sample holder and the manifold. After the other end of the fibers has been accommodated, at process step S105, a sealed fiber optic interface between the sample holder and the optics portion is formed. After the sample has been tested, the process proceeds to decision step S106 where it is determined whether another sample is to be tested. If another sample is to be tested, the process returns to process step S101, otherwise, the process terminates at state S107.

The fiber optic detection system can be used with any optical detection method. In some embodiments, the fiber optic detection system can be used to detect a biological sample. The biological sample being detected can be a protein, peptide, nucleic acid (e.g., DNA, RNA, cDNA, etc.), carbohydrate, virus, or bacteria, for example. These sample being detected may be indicative of a particular biological agent. For example, the presence of anthrax or plague can be detected by detecting nucleic acids indicative of these biological threats. The biological samples can be detected using any suitable methods, including immunological methods, labeled antibodies, and nucleic acid probes. For example, a nucleic acid probe can be used to detect a nucleic acid. The nucleic acid probe may be used in conjunction with a dye or fluorphore that emits light indicating the presence or absence of the target sequence. The nucleic acid probes can be any type of nucleic acid probes, including molecular beacon probes, linear probes, hairpin probes, and the probes described in U.S. patent application Ser. No. 11/252,433, filed 17 Oct. 2005, which is hereby incorporated by reference. As another example, a protein can be detected using a fluorescently labeled antibody. The fiber optic detection system can detect the presence of a protein by detecting the fluorescence of the antibody that specifically binds the protein. In some embodiments, multiple proteins can be detected simultaneously using antibodies with differing specificities and emission wavelengths. The use of the fiber optic detection system to detect biological samples can be advantageous, because the ease with which the system can be detected allows its easy use with even extremely dangerous samples.

Embodiments for the sealed and decontaminated fiber optic detection apparatus used for a PCR discussed above have several advantages and benefits. First, a single modular optical block containing multiple source and emission optical components is realized with this arrangement. Thus, each optical train of active components, filters, and lenses are housed in a single bore for superior alignment. Also with this arrangement, the use of fiber in the manifold allows for rapid assembly and avoidance of miscoupling of the fiber with an emitter or detector location. Finally, with this arrangement, full decontamination of the reaction chamber without degrading any of the optical and electro-optical components is realized since the fiber is sealed between the reaction chamber and the optics block.

Some exemplary embodiments have been described. However substitutions, modifications, changes and omissions can be made in the design, operating configuration and arrangement of the preferred and other exemplary embodiments without departing from the scope and spirit of the appended claims.

What is claimed is:

1. A detection apparatus comprising:
   an optics portion comprising individual chambers;
   a manifold;
   a sample holder configured to hold a sample to be tested; and
   a mounting device;
   wherein
   at least one of the individual chambers comprises a sample portion and at least one of another of the individual chambers comprises an excitation portion;
   the sample portion and the excitation portion include optical and electro-optical components;
   the manifold is configured to accommodate fibers in optical communication with the sample portion and excitation portion.

2. The detection apparatus according to claim 1, further comprising a mounting device, wherein the mounting device and the manifold form a sealed fiber optic interface between the sample holder and the optics portion.

3. The detection apparatus according to claim 1, wherein the excitation portion includes a light source.

4. The detection apparatus according to claim 3, wherein the light source is a light emitting diode.

5. The detection apparatus according to claim 1, wherein the sample portion includes a light detector.

6. The detection apparatus according to claim 5, wherein the light detector is a photodiode.

7. The detection apparatus according to claim 1, wherein the sample portion and the excitation portion are contained within a single bore of the optics portion defining the individual chambers.

8. The detection apparatus according to claim 1, further comprising fibers integrated into the manifold.

9. The detection apparatus according to claim 1, wherein the sample holder includes an optical window.

10. The detection apparatus according to claim 1, further comprising a heat sink provided adjacent to the mounting device.

11. The detection apparatus according to claim 1, wherein the manifold is detachably mounted to one end of the optics portion.

12. The detection apparatus according to claim 1, wherein the manifold is sealed to one end of the optics portion.

13. The detection apparatus according to claim 10, wherein the heat sink is provided on an opposite side of where the sample is being tested.

14. The s detection apparatus according to claim 1, further comprising lenses in the individual chambers to focus light onto or from fibers.

15. The detection apparatus according to claim 1, wherein the manifold is configured to accommodate more than two fibers in optical communication with the sample portion and excitation portion.

16. A method for creating a detection apparatus, comprising:

housing optical and electro-optical components in individual chambers of an optics portion;

accommodating one end of fibers, which are in optical communication with the optical and electro-optical components, in a manifold;

providing a sample holder configured to hold a sample to be tested;

accommodating the other end of the fibers between the sample holder and the manifold; and forming a sealed fiber optic interface between the sample holder and the optics portion.

17. The method for creating a detection apparatus according to claim 16, further comprising detachably mounting the manifold to one end of the optics portion.

18. The method for creating a detection apparatus according to claim 16, further comprising sealing the manifold to one end of the optics portion.

19. The method for creating a detection apparatus according to claim 16, further comprising integrating the fibers into the manifold.

20. The method for creating a detection apparatus according to claim 16, further comprising providing a heat sink opposite to the sample to be tested.

21. A detection system, comprising:

an optics portion with individual chambers, the chambers housing optical and electro-optical components;

a manifold accommodating fibers, each of the fibers being in optical communication with the optical and electro-optical components of a corresponding chamber;

a sample holder that holds a sample to be tested;

a mounting device provided between the sample holder and the manifold; and a printed circuit board connected to the mounting device, wherein the mounting device and the manifold form a sealed fiber optic interface between the sample holder and the optics portion.

\* \* \* \* \*

UNITED STATES PATENT AND TRADEMARK OFFICE
CERTIFICATE OF CORRECTION

| | | |
|---|---|---|
| PATENT NO. | : 7,933,011 B2 | Page 1 of 1 |
| APPLICATION NO. | : 12/172142 | |
| DATED | : April 26, 2011 | |
| INVENTOR(S) | : Douglas J. Green et al. | |

It is certified that error appears in the above-identified patent and that said Letters Patent is hereby corrected as shown below:

Column 8, claim 14, line 59-61 should read: --The detection apparatus according to claim 1, further comprising lenses in the individual chambers to focus light onto or from fibers.--

Signed and Sealed this
Ninth Day of August, 2011

David J. Kappos
*Director of the United States Patent and Trademark Office*